United States Patent [19]

Sherwin et al.

[11] Patent Number: 5,008,428

[45] Date of Patent: * Apr. 16, 1991

[54] INTEGRATED PROCESS FOR THE PRODUCTION OF AMINOACETONITRILES

[75] Inventors: Martin B. Sherwin, Potomac; Jow-Lih Su, Silver Spring, both of Md.

[73] Assignee: W. R. Grace & Co.-Conn., New York, N.Y.

[*] Notice: The portion of the term of this patent subsequent to Jan. 23, 2007 has been disclaimed.

[21] Appl. No.: 425,438

[22] Filed: Oct. 26, 1989

[51] Int. Cl.$^5$ .......................................... C07C 253/30
[52] U.S. Cl. ................................................... 558/346
[58] Field of Search ......................................... 558/346

[56] References Cited

U.S. PATENT DOCUMENTS

| | | |
|---|---|---|
| 2,604,380 | 10/1946 | Beekhuis ............................... 23/151 |
| 2,794,044 | 5/1957 | Miller ................................... 558/346 |
| 3,061,628 | 10/1962 | Singer, Jr. et al. ................. 558/346 |
| 3,167,580 | 1/1965 | Saunders et al. .................... 558/346 |
| 3,337,607 | 8/1967 | Wollensak ............................ 558/346 |
| 3,415,878 | 12/1968 | Gaunt ................................... 260/534 |
| 3,714,335 | 1/1973 | Kobetz et al. ....................... 423/483 |
| 3,840,581 | 10/1974 | Neumaier et al. ................... 558/346 |
| 3,856,844 | 12/1974 | Wikman ............................... 558/346 |
| 3,862,203 | 1/1975 | Greco et al. ......................... 558/346 |
| 3,864,378 | 2/1975 | Homberg et al. ................... 558/346 |
| 3,907,858 | 9/1975 | Davis et al. ......................... 558/346 |
| 3,925,448 | 12/1975 | Lanier ................................. 558/346 |
| 3,950,384 | 4/1976 | Neumaier et al. ................... 558/346 |
| 3,959,342 | 5/1977 | Homberg et al. ................... 558/346 |
| 3,984,453 | 10/1976 | Chaberek ............................. 558/346 |
| 3,988,360 | 10/1976 | Gaudette et al. .................... 558/346 |
| 3,993,681 | 11/1976 | Cullen ................................. 558/346 |
| 4,307,037 | 12/1981 | Suchsland et al. .................. 558/346 |
| 4,478,759 | 10/1987 | Distler et al. ....................... 558/346 |
| 4,485,049 | 11/1984 | Lannert et al. ..................... 558/346 |
| 4,543,215 | 9/1985 | Brunnmueller et al. ........... 558/346 |
| 4,661,614 | 4/1987 | Most et al. .......................... 558/346 |
| 4,731,465 | 3/1988 | Shen et al. .......................... 558/346 |
| 4,745,207 | 5/1988 | Brunnmueller et al. ........... 558/351 |
| 4,895,971 | 1/1990 | Su et al. ............................... 558/346 |

FOREIGN PATENT DOCUMENTS 102343 3/1984 European Pat. Off. .
102935 3/1984 European Pat. Off. .

OTHER PUBLICATIONS

Kirk–Othmer Encyclopedia of Chemical Technology, 2nd Ed., vol. 6 "Cyanides (Hydrogen Cyanides)", pp. 582–583 (1965).

Primary Examiner—Joseph Paul Brust
Attorney, Agent, or Firm—James P. Barr

[57] ABSTRACT

This invention relates to the production of aminoacetonitriles, and more specifically to an integrated process wherein a crude, unpurified reactor product stream from a hydrogen cyanide reactor together with a formaldehyde stream, optionally, a crude, unpurified reactor product stream from a formaldehyde process reactor are fed directly to a reactive absorber with an additional nitrogen source and scrubbed with a controlled pH aqueous solution to produce aminoacetonitriles in high yields. This process eliminates intermediate recovery and purification processes associated with conventional hydrogen cyanide and formaldehyde production processes by integrating the recovery and reaction processes into a reactive absorber.

20 Claims, No Drawings

INTEGRATED PROCESS FOR THE PRODUCTION OF AMINOACETONITRILES

BACKGROUND OF THE INVENTION

1. Field of the Invention

This invention is related to application Ser. No. 264,413, filed Oct. 31, 1988. This invention relates to the production of aminoacetonitriles, and more specifically to an integrated process wherein a crude, unpurified hydrogen cyanide product gas stream from a hydrogen cyanide process reactor together with a formaldehyde stream, optionally, a crude, unpurified formaldehyde product gas stream from a formaldehyde process reactor, are fed directly into a reactive absorber, together with an additional nitrogen source and scrubbed with a controlled-pH, aqueous solution to produce aminoacetonitriles in high yields. This process provides improved economics for the production of aminoacetonitriles by eliminating the costly recovery and purification processes associated with conventional hydrogen cyanide and formaldehyde production processes.

2. Background

It is known in the prior art that aminoacetonitriles can be prepared by reacting formaldehyde and hydrogen cyanide together with a nitrogen source in liquid phase. For example, nitriloacetonitrile can be produced by this method as shown in the following general reaction:

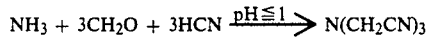

$$NH_3 + 3CH_2O + 3HCN \xrightarrow{pH \leq 1} N(CH_2CN)_3$$

Similarly, EP 0 102 343 A1 teaches a process for producing nitrilotriacetonitrile from an ammonia derivative, formaldehyde and hydrogen cyanide. In this process hydrogen cyanide is scrubbed from a gas stream with an aqueous solution containing nitrilotriacetonitrile mother liquor to produce a hydrogen cyanide containing solution. To this hydrogen cyanide containing solution is added formaldehyde and an ammonia derivative selected from the group consisting of ammonia, an ammonium salt, and hexamethylenetetraamine to produce a reaction mixture. This reaction mixture is then reacted to produce nitrilotriacetonitrile in approximately 88-97.5% yields.

EP 0,102,935 teaches a process for producing nitrilotriacetonitrile from an ammonia derivative, formaldehyde and hydrogen cyanide. In this process the hydrogen cyanide is scrubbed from a gas stream containing hydrogen cyanide with a dilute solution of a mineral acid to produce a hydrogen cyanide containing solution. To this hydrogen cyanide containing solution is added an ammonia derivative selected from the group consisting of ammonia, an ammonium derivative, and hexamethylenetetramine to produce a reaction mixture. This reaction mixture is then reacted to produce nitrilotriacetonitrile.

On an industrial scale, the conventional processes for the production of aminoacetonitriles require purified, commercial grade liquid hydrogen cyanide and formaldehyde in high concentration in order to obtain product in high enough yield to warrant economic feasibility. Substantial engineering considerations and capital equipment costs can be attributed to the recovery and purification equipment required to obtain commercially pure formaldehyde and hydrogen cyanide. For example, in the production of hydrogen cyanide, the crude product gas stream contains, in addition to hydrogen cyanide, a significant amount of ammonia. In conventional manufacturing methods the ammonia must always be removed to avoid the dangerous exothermic polymerization of the liquid hydrogen cyanide.

Similarly, in the production of formaldehyde, the crude reactor product stream is a dilute gaseous mixture of formaldehyde and water which requires large absorption columns to recover formaldehyde in sufficient purity.

It has now been discovered that aminoacetonitriles can be produced using crude, unpurified gaseous product streams from formaldehyde and hydrogen cyanide reactors directly without the need of purifying these reactive product streams. Under the process of this invention, it is no longer necessary, and is actually redundant to remove the unreacted ammonia gas from the hydrogen cyanide product gas stream as a purification step, only to add it later in the downstream production of aminoacetonitriles. This also applies to the excess water in each of the hydrogen cyanide and formaldehyde processes. That is, since the reactants in the aminoacetonitrile production process must be diluted in water prior to their reactions, it is redundant to remove water from the crude unpurified reactor product streams.

SUMMARY OF THE INVENTION

An object of this invention is to provide a new and improved process for the production of aminoacetonitriles.

A further object of this invention is to provide a simple integrated process for the production of aminoacetonitriles.

A further object of this invention is to provide an improved process for the production of aminoacetonitriles wherein conventional upstream reactant purification processes are eliminated.

Under the process of this invention, it has been discovered that aminoacetonitriles can be produced by an integrated process wherein the direct, unpurified hydrogen cyanide product gas stream from a hydrogen cyanide process reactor comprising a mixture of hydrogen cyanide and ammonia and a formaldehyde stream, optionally a crude, unpurified product gas stream from a formaldehyde process reactor, together with an additional nitrogen source, are contacted under reactive conditions to produce aminoacetonitrile in high yields.

These and other objects will be apparent from the remaining specification and the appended claims.

DETAILED DESCRIPTION

The subject process is directed to a means of producing aminoacetonitriles by integrating the gaseous product streams from the production processes of hydrogen cyanide and formaldehyde into a simple one-step aminoacetonitrile formation process, thereby eliminating conventional formaldehyde and hydrogen cyanide purification and recovery processes.

Specifically, under the process of this invention, two reactant streams, one containing an unpurified, crude hydrogen cyanide product stream comprising a gaseous mixture of hydrogen cyanide and unreacted ammonia, the other containing formaldehyde, optionally a crude, unpurified gas stream from a formaldehyde process reactor comprising a gaseous mixture of formaldehyde, water and unreacted methanol, together with an additional nitrogen source, are scrubbed in a reactive absorber with an aqueous, controlled pH solution to produce aminoacetonitriles. Under this process, reactant recovery as well as reaction are performed in the same reactive absorber. The two reactant streams may be introduced into the reactive absorber through separate feed streams, or optionally, the reactant streams may be mixed together prior to being fed into the reactive absorber. When those reactant streams are pre-mixed, it is believed that glycolonitrile is formed as an intermediate. Suitable types of reactive absorbers include, but are not limited to, bubble column, packed column, tray column and the like, and is preferably a bubble column. Furthermore, for flexibility of engineering design, an optional additional reactor may be added downstream from the reactive absorber, in order to accelerate the nitrile formation reaction that was initiated in the reactive absorber. This reactor may be in the form of a stir tank or a hot tube and is preferably a hot tube. The hot tube is typically maintained at a temperature in the range 50° to 200° C. and a reactant residence time in the range 10 seconds to 1 hour. Various other reactor types are well known to those skilled in the art, and a choice of a particular reactor is not critical, per se, to this invention.

Those processes capable of forming reactant hydrogen cyanide streams suitable for use in this invention include: the ammoxidation of methane (Andrussow Process or the Degussa process, also called the BMA process), the reaction of ammonia and propane (Fluohmic process), the ammoxidation of methanol, the decomposition of formamide, and the recovery of hydrogen cyanide as the by-product in the preparation of acrylonitrile by the ammoxidation of propylene (SOHIO process). These and other similar processes are well documented in the art. Since all of these processes use ammonia as the source of nitrogen, the product gas streams will contain a mixture of unreacted ammonia and hydrogen cyanide. Contemplated equivalents are those processes that are simple variations of the given examples but produce a crude unpurified hydrogen cyanide product stream containing an excess of unreacted ammonia or related nitrogen source.

A suitable process for the production of a crude, unpurified formaldehyde reactant stream is by the catalytic dehydrogenation of methanol over a silver catalyst (BASF process). The reaction is endothermic, and may be written as follows:

$$CH_3OH \rightleftharpoons CH_2O + H_2$$ 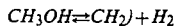

Another suitable process to prepare a crude formaldehyde reactant stream is by the oxidation of methanol by a metal oxide catalyst such as ferric molybdate. This reaction using a ferric molybdate catalyst is exothermic, and may be written as follows:

$$CH_3OH + \tfrac{1}{2}O_2 \rightarrow CH_2O + H_2O$$ 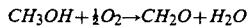

These crude formaldehyde product streams may be introduced directly into the reactive absorber, or they may first be fed into an aqueous absorption column where formaldehyde is recovered as an aqueous solution, and then introduced into the reactive absorber.

The additional sources of nitrogen capable of being used in this process can be represented by the formula

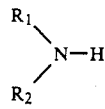

wherein $R_1$ and $R_2$ are each independently selected from alkyl, alkene, or cycloalkyl group and their amine substituted derivatives or hydrogen, preferably a $C_1$ to $C_{20}$ alkyl or alkene and most preferably a $C_1$ to $C_3$ alkyl or alkene group. Examples of suitable nitrogen sources include, but are not limited to ammonia, methylamine, ethylamine, n-propylamine, isopropylamine, n-butylamine, isobutylamine, sec.-butylamine, tert.-butylamine, pentylamine, pentyl-2-amine, pentyl-3-amine, n-hexylamine, n-heptylamine, n-octylamine, n-nonylamine, n-decylamine and 2-ethylhexylamine; ethylenediamine, propylenediamine, isopropylenediamine, butylenediamine, sec.-butylenediamine, isobutylenediamine and tert.-butylenediamine; diethylenetriamine, dipropylenetriamine, diisopropylenetriamine, dibutylenetriamine, diisobutylene-triamine, di-sec.-butylenetriamine and ditert.-butylene-triamine; triethylenetetramine, tripropylenetetramine, triisopropylenetetramine, tributylenetetramine, tri-sec.-butylenetetramine, triisobutylenetetramine and tri-tert.-butylenetetramine; tetraethylenepentamine, tetra-propylenepentamine, tetraisopropylenepentamine, tetrabutylenepentamine, tetraisobutylenepentamine, tetra-sec.-butylenepentamine and tetra-tert.-butylenepentamine.

A first embodiment of this invention is directed to a process for the preparation of nitrilotriacetonitrile. In this embodiment a crude, unpurified hydrogen cyanide product stream and a formaldehyde stream, optionally a crude unpurified formaldehyde product stream, are produced in respective upstream reactors by one of the previously disclosed processes and are fed into a reactive absorber together with an additional gaseous or liquid ammonia or hexamethylenetetramine stream (HMTA) and scrubbed with an acidified aqueous solution. The reactive absorber is maintained at a temperature between 25° and 90° C., and preferably between 60° and 85° C. The pressure of the reactive absorber is maximized to enhance absorption and is typically maintained in the range 5 to 200 psig. The scrubbing solution is an acidified aqueous solution, and may contain recycled nitrilotriacetonitrile. Any acid can be used in the scrubbing solution to control the pH and is typically sulfuric acid. The acidified aqueous scrubbing solution is maintained at a pH in the range 0.1 to 2.0, and preferably in the range 0.1 to 0.5, by the continuous addition of acid.

A second embodiment of this invention is directed to a process for the preparation of ethylenediaminetetraacetonitrile (EDTN). In this embodiment a crude, unpurified hydrogen cyanide product stream and a formaldehyde stream, optionally a crude, unpurified formaldehyde product stream are produced in respective upstream reactors. The product streams are fed directly into a reactive absorber together with a gaseous or liquid ethylenediamine stream and scrubbed with an acidified aqueous solution. The reactive absorber is maintained at a temperature in the range 50° to 90° C. and is preferably between 60° to 85° C. The pressure of the reactive absorber is maximized to enhance absorption and is typically in the range 5 to 200 psig. The acidified aqueous scrubbing solution is maintained, by the continuous addition of acid, at a pH in the range 0.1 to 2.0 and preferably 0.5 to 1.0, and may also contain some recycled EDTN.

A third embodiment of this invention is directed to a process for the preparation of glycinonitrile. In this embodiment a crude, unpurified hydrogen cyanide product stream and a formaldehyde stream, optionally a crude, unpurified formaldehyde product stream are produced in respective upstream reactors. The product streams are fed directly into a reactive absorber together with an additional gaseous or liquid ammonia stream and scrubbed with an alkaline aqueous solution at a temperature in the range 25° to 85° C. The scrubbing solution is an aqueous alkaline solution maintained at a pH in the range 8 to 12, preferably in the range 9 to 11, by the continuous addition of ammonia. The scrubbing solution may also contain some recycled glycinonitriles. The reaction mixture, which may contain glycolonitrile may optionally be pumped through a hot tube at a temperature in the range 60° to 100° C. to accelerate the production of glycinonitrile.

The following examples are provided to illustrate the invention in accordance with the principles of this invention, but are not to be construed as limiting the invention in any way except as indicated in the appended claims. All parts and precentages are by moles unless otherwise indicated.

EXAMPLE 1

This example describes the preparation of nitrilotriacetonitrile in accordance with the process of this invention. Hydrogen cyanide and formaldehyde streams were generated in upstream reactors by methanol ammoxidation and methanol oxidation respectively. The crude, unpurified gaseous hydrogen cyanide product stream contained approximately 3–5% hydrogen cyanide with a total flow rate of approximately 10–11 moles per hour. The crude, gaseous formaldehyde stream contained approximately 4–5% formaldehyde with a total flow rate of approximately 10–11 moles per hour. These crude gaseous product streams were fed directly into a bubble column reactive absorber containing a scrubber solution containing 1500 g of water, acidified to a pH in the range 0.1 to 0.5 with about 200 g of sulfuric acid. An additional nitrogen source was also fed to the scrubber e.g. ammonia or HMTA, for the nitrilotriacetonitrile formation. The amount of hydrogen cyanide and formaldehyde recovered in the scrubber varied depending on the scrubber conditions. Typically the hydrogen cyanide recovery was between 61–85% and the formaldehyde recovery was greater than 98%. The reactive absorber solution was recycled with continuous addition of sulfuric acid to maintain a constant pH of about 0.1 to 0.5, and to remove excess water. The reactive absorber was maintained at a temperature of 60° to 85° C. and at a pressure of 10 to 20 psig. Every five hours the scrubbing solution was completely withdrawn, cooled, and filtered to remove the solid nitriles. The filtrate was then charged back into the scrubber for further reaction. This experiment was run for approximately 15 to 20 hours.

Experimental Conditions and Results

| Experiment No. | pH | Temp. °C. | Pressure (psig) | Total reactants recov'd | | | | Total NTAN formed (Moles) | Yield Based on HCN (%) |
| --- | --- | --- | --- | --- | --- | --- | --- | --- | --- |
| | | | | CH$_2$O | HCN | HN$_3$ | HMTA | | |
| 1 | 0.1 | 60–70 | 10 | 4.9 | 3.3 | 1.0 | — | 0.29 | 26 |
| 2 | 0.1 | 60–70 | 10 | 4.8 | 4.9 | 1.8 | — | 0.42 | 26 |
| 3 | 0.5 | 60–70 | 10 | 8.6 | 7.6 | 2.3 | — | 0.56 | 28 |
| 4 | 0.1–0.3 | 85 | 20 | 8.5 | 7.0 | 2.4 | — | 0.39 | 17 |
| 5 | 0.1–0.3 | 70 | 20 | 4.5 | 5.4 | — | 0.45 | 0.91 | 51 |

EXAMPLE 2

This example describes the preparation of ethylenediaminetetraacetonitrile in accordance with the process of this invention. Hydrogen cyanide and formaldehyde streams were generated in upstream reactors by methanol ammoxidation and methanol oxidation respectively as described in Example 1. The crude, unpurified, product gas streams from these reactors were fed directly into a bubble column reactive absorber containing 1500 g of water acidified to a pH of 0.8, together with an additional stream of ethylenediamine (EDA). The reactive absorber solution was recycled with continuous addition of sulfuric acid to maintain a constant pH of about 0.8. The reactive absorber was maintained at a temperature of 60° C. and at a pressure of 0 psig. The results are summarized as follows:

| Total Recovered Reactants in Reactive Absorber (moles) | | | Total EDTN formed (moles) | EDTN Yield (%) based on: | | |
| --- | --- | --- | --- | --- | --- | --- |
| EDA | CH$_2$O | HCN | | EDA | CH$_2$O | HCN |
| 1.0 | 3.9 | 3.8 | 0.24 | 24 | 25 | 25 |

EXAMPLE 3

This example describes the preparation of glycinonitrile in accordance with the process of this invention. In this example, a separate absorption/reaction scheme was used. Hydrogen cyanide and formaldehyde product streams were generated in upstream reactors by methanol ammoxidation and methanol oxidation respectively as described in Example 1. The crude, unpurified gaseous product streams from these reactors were fed directly into a bubble column, together with an additional stream of ammonia and scrubbed with an ammonia-water solution. The reactive absorber solution was recycled with the continuous addition of ammonia to maintain a constant pH of about 10.0 to about 10.7. The reactive absorber was maintained at a temperature of 25° to 30° C. and a pressure of 4 psig. Hydrogen cyanide was completely recovered in a 4 ft. column. This suggested that the absorption was enhanced by chemical reaction, most likely by the formation of glycolonitrile.

In the ensuing reaction step, the reaction mixture from the scrubber was pumped through a hot tube at 80° C. for 5 to 10 minutes where glycinonitrile was produced. The results are summarized as follows:

TABLE 3

| | | Production of Glycinonitrile | | |
|---|---|---|---|---|
| Absorption Step | Scrubbing Liquid | 1500 g $H_2O$ | 1500 g $H_2O$ | 1500 g $H_2O$ |
| | Gas Feed Compositing | HCN = 1.6 mol % | HCN = 1.6 mol % | HCN = 1.6 mol % |
| | | $CH_2O$ = 1.7 mol % | $CH_2O$ = 1.7 mol % | $CH_2O$ = 1.7 mol % |
| | | $NH_3$ = 4.6 mol % | $NH_3$ = 6.8 mol % | $NH_3$ = 8.9 mol % |
| | Liquid/Vapor Molar Ratio | 1.6 | 1.6 | 1.6 |
| | Temperature, °C. | 27 | 27 | 27 |
| | Pressure, psig | 4 | 4 | 4 |
| Reaction Step | Temperature, °C. | 80 | 80 | 80 |
| | Res. Time, min. | 6.2 | 6.2 | 6.2 |
| | pH | 10.2 | 10.5 | 10.7 |
| | $NH_3$/HCN Molar Ratio | 2.9 | 4.2 | 5.6 |
| Glycinonitrile | Based on HCN | 84.0 | 87.5 | 82.8 |
| Yield, % | Based on $CH_2O$ | 79.4 | 82.4 | 77.9 |

What is claimed is:

1. An improved process for the production of aminoacetonitriles prepared by
    (a) contacting in a reactive absorber, under reactive conditions hydrogen cyanide, formaldehyde, and an additional nitrogen source,
    (b) scrubbing the reaction products from (a) supra with a pH-controlled, aqueous scrubbing solution to form an aminoacetonitrile product, and
    (c) recovering the product,
wherein the improvement comprises:
    using as a source of hydrogen cyanide in step (a) the direct unpurified reactor product stream of a hydrogen cyanide production process comprising a gaseous mixture of hydrogen cyanide and ammonia, using as a source of formaldehyde in step (a) the direct unpurified reactor product stream of a formaldehyde production process comprising a gaseous mixture of formaldehyde and water using as an additional nitrogen source a composition represented by the formula

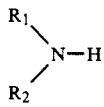

wherein $R_1$ and $R_2$ are each independently selected from alkyl, alkene, cycloalkyl groups, their amine substituted derivatives, and hydrogen.

2. An improved process for the production of aminoacetonitriles prepared by
    (a) contacting in a reactive absorber, under reactive conditions hydrogen cyanide, formaldehyde, and an additional nitrogen source,
    (b) scrubbing the reaction products from (a) supra with a pH-controlled, aqueous scrubbing solution to from an aminoacetonitrile product, and
    (c) recovering the product,
wherein the improvement comprises:
    using as a source of hydrogen cyanide in step (a) the direct unpurified reactor product stream of a hydrogen cyanide production process comprising a gaseous mixture of hydrogen cyanide and ammonia, using as a source of formaldehyde in step (a) the aqueous formaldehyde solution obtained from an absorption column of a formaldehyde production process using as an additional nitrogen source a composition represented by the formula

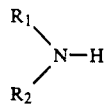

wherein $R_1$ and $R_2$ are each independently selected from alkyl, alkene, cycloalkyl groups, their amine substituted derivatives, and hydrogen.

3. The improved process for the production of aminoacetonitriles in claim 1 wherein the process for producing the unpurified hydrogen cyanide reactor product gas stream is the ammoxidation of methane, the ammoxidation of methanol, the reaction of ammonia and propane, the decomposition of formamide, the recovery of hydrogen cyanide from the ammoxidation of propylene, or the process wherein methanol or formaldehyde or a mixture thereof, ammonia and oxygen are reacted in the presence of a metal oxide catalyst simultaneously with the decomposition of formamide.

4. The improved process for the production of aminoacetonitriles in claim 1 wherein the process for producing the crude formaldehyde reactor product stream is the catalytic oxidation of methanol over ferric molybdate or the catalytic dehydrogenation of methanol over a silver catalyst.

5. The improved process for the production of aminoacetonitriles according to claim 1 wherein the reactive absorber is maintained at a pressure in the range 5 to 200 psig., at a temperature 50° C., the aqueous scrubber solution has a pH in the range of 0.1 to 2.0, the pH being maintained by the continuous addition of a mineral acid, and additional nitrogen source is ethylenediamine, and wherein the aminoacetonitrile product is ethylenediamine-tetraacetonitrile.

6. The improved process for the production of ethylenediaminatetraacetonitrile in claim 5 wherein:
    (a) the reactive absorber is maintained;
        (1) at a temperature in the range 60° to 85° C.;
        (2) at a pressure in the range 5 to 100 psig
    (b) the pH of the aqueous scrubber solution is maintained in the range of 0.5 to 1.0 by the continuous addition of $H_2SO_4$.

7. The improved process for the production of aminoacetonitriles according to claim 2 wherein the reactive absorber is maintained at a pressure in the range 5 to 200 psig., at a temperature 50° to 90° C., the aqueous scrubber solution has a pH in the range of 0.1 to 2.0, the pH being maintained by the continuous addition of a mineral acid, and the additional nitrogen source is ethylenediamine, and wherein the aminoacetonitrile product is ethylenediamine-tetraacetonitrile.

8. The improved process for the production of aminoacetonitriles according to claim 1 wherein
(a) the reactive absorber is maintained:
(a) at a pressure in the range 10 to 200 psig. at a temperature in the range 25° to 90° C.,
(b) the pH of the aqueous scrubber solution is maintained in the range 0.1 to 1.0 by the continuous addition of H2SO4
and the additional nitrogen source is ammonia and wherein the aminoacetonitrile product is nitrilotriacetonitrile.

9. The improved process for the production of aminoacetonitriles according to claim 1 wherein
(a) the reactive absorber is maintained
(1) at a temperature in the range 60° to 85° C.;
(2) at a pressure in the range 50 to 200 psig
(b) the pH of the aqueous scrubber solution is maintained in the range 0.1 to 0.5 by the continuous addition of H2SO4
and the additional nitrogen source is ammonia and wherein the aminoacetonitrile product is nitrilotriacetonitrile.

10. The improved process for the production of aminoacetonitriles according to claim 2 wherein
(a) the reactive absorber is maintained:
(a) at a pressure in the range 10 to 200 psig. at a temperature in the range 25° to 90° C.,
(b) the pH of the aqueous scrubber solution is maintained in the range 0.1 to 1.0 by the continuous addition of H2SO4
and the additional nitrogen source is ammonia and wherein the aminoacetonitrile product is nitrilotriacetonitrile.

11. The improved process for the production of aminoacetonitriles according to claim 1 wherein
(a) the reactive absorber is maintained:
(a) at a pressure in the range 1 to 10 psig. at a temperature in the range 25° to 90° C.,
(b) the pH of the aqueous scrubber solution is maintained in the range 8 to 12 by the continuous addition of H2SO4
and the additional nitrogen source is ammonia and wherein the aminoacetonitrile product is glycinonitrile.

12. The improved process for the production of aminoacetonitriles in claim 1 wherein
(a) the reactive absorber is maintained
(1) at a temperature in the range 60° to 85° C.;
(2) at a pressure in the range 5 to 10 psig
(b) the pH of the aqueous scrubber solution is maintained in the range 9 to 11 by the continuous addition of H2SO4
and the additional nitrogen source is ammonia and wherein the aminoacetonitrile product is glycinonitrile.

13. The improved process for the production of aminoacetonitriles according to claim 2 wherein
(a) the reactive absorber is maintained;
(a) at a pressure in the range 1 to 10 psig. at a temperature in the range 25° to 90° C.,
(b) the pH of the aqueous scrubber solution is maintained in the range 8 to 12 by the continuous addition of H2SO4
and the additional nitrogen source is ammonia and wherein the aminoacetonitrile product is glycinonitrile.

14. The improved process for the production of glycinonitrile according to claim 12 wherein the glycinonitrile product stream is passed through a hot tube reactor.

15. An improved process for the production of aminoacetonitriles prepared by
(a) contacting in a reactive absorber, under reactive conditions hydrogen cyanide, formaldehyde, and an additional nitrogen source,
(b) scrubbing the reaction products from (a) supra with a pH-controlled, aqueous scrubbing solution to form an aminoacetonitrile product, and
(c) recovering the product,
wherein the improvement comprises:
using as a source of hydrogen cyanide in step (a) the direct unpurified reactor product stream of a hydrogen cyanide production process comprising a gaseous mixture of hydrogen cyanide and ammonia,
using as a source of formaldehyde in step (a) the direct unpurified reactor product stream of a formaldehyde production process comprising a gaseous mixture of formaldehyde and water, using as an additional nitrogen source a composition represented by the formula

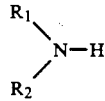

wherein $R_1$ and $R_2$ are each independently selected from alkyl, alkene, cycloalkyl groups, their amine substituted derivatives, and hydrogen
and wherein the aminoacetonitrile product from step (b) is passed through a hot tube reactor maintained at a temperature in the range 50° to 200° C. to accelerate nitrile formation.

16. An improved process for the production of aminoacetonitriles prepared by
(a) contacting in a reactive absorber, under reactive conditions hydrogen cyanide, formaldehyde, and an additional nitrogen source,
(b) scrubbing the reaction products from (a) supra with a pH-controlled, aqueous scrubbing solution to form an aminoacetonitrile product, and
(c) recovering the product,
wherein the improvement comprises:
using as a source of hydrogen cyanide in step (a) the direct unpurified reactor product stream of a hydrogen cyanide production process comprising a gaseous mixture of hydrogen cyanide and ammonia,
using as a source of formaldehyde in step (a) the aqueous formaldehyde solution obtained from an absorption column of a formaldehyde production process,
and wherein the aminoacetonitrile product from step (b) is passed through a hot tube reactor maintained at a temperature in the range 50° to 200° C. to accelerate nitrile formation using as an additional nitrogen source a composition represented by the formula

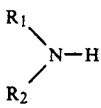

wherein R₁ and R₂ are each independently selected from alkyl, alkene, cycloalkyl groups, their amine substituted derivatives, and hydrogen.

17. An improved process according to claim 1 wherein the additional nitrogen source is selected from the group consisting of ammonia, methylamine, ethylamine, n-propylamine, isopropylamine, n-butylamine, isobutylamine, sec-butylamine, tert-butylamine, pentylamine, pentyl-2-amine, pentyl-3-amine, n-hexylamine, n-heptylamine, n-octylamine, n-nonylamine, n-decylamine and 2-ethylhexylamine; ethylenediamine, propylenediamine, isopropylenediamine, butylenediamine, sec-butylenediamine, isobutylenediamine and tert-butylenediamine; diethylenetriamine, dipropylenetriamine, diisopropylenetriamine, dibutylenetriamine, diisobutylenetriamine, di-sec-butylenetriamine and di-tert-butylenetriamine; triethylenetetramine, tripropylenetetramine, triisopropylenetetramine, tributylenetetramine, tri-sec-butylenetetramine, triisobutylenetetramine and tri-tert-butylenetetramine; tetraethylenepentamine, tetrapropylenepentamine, tetraisopropylenepentamine, tetrabutylenepentamine, tetraisobutylenepentamine, tetra-sec-butylenepentamine and tetra-tert-butylenepentamine.

18. An improved process according to claim 2 wherein the additional nitrogen source is selected from the group consisting of ammonia, methylamine, ethylamine, n-propylamine, isopropylamine, n-butylamine, isobutylamine, sec-butylamine, tert-butylamine, pentylamine, pentyl-2-amine, pentyl-3-amine, n-hexylamine, n-heptylamine, n-octylamine, n-nonylamine, n-decylamine and 2-ethylhexylamine; ethylenediamine, propylenediamine, isopropylenediamine, butylenediamine, sec-butylenediamine, isobutylenediamine and tert-butylenediamine; diethylenetriamine, dipropylenetriamine, diisopropylenetriamine, dibutylenetriamine, diisobutylenetriamine, de-sec-butylenetriamine and di-tert-butylenetriamine; triethylenetetramine, tripropylenetetramine, triisopropylenetetramine, tributylenetetramine, tri-sec-butylenetetramine, triisobutylenetetramine and tri-tertbutylenetetramine; tetraethylenepentamine, tetra-propylenepentamine, tetraisopropylenepentamine, tetrabutylenepentamine, tetraisobutylenepentamine, tetra-sec-butylenepentamine and tetra-tert-butylenepentamine.

19. An improved process according to claim 15 wherein the additional nitrogen source is selected from the group consisting of ammonia, methylamine, ethylamine, n-propylamine, isopropylamine, n-butylamine, isobutylamine, sec-butylamine, tert-butylamine, pentylamine, pentyl-2-amine, pentyl-3-amine, n-hexylamine, n-heptylamine, n-octylamine, n-nonylamine, n-decylamine and 2-ethylhexylamine; ethylenediamine, propylenediamine, isopropylenediamine, butylenediamine, sec-butylenediamine, isobutylenediamine and tert-butylenediamine; diethylenetriamine, dipropylenetriamine, diisopropylenetriamine, dibutylenetriamine, diisobutylenetriamine, di-sec-butylenetriamine and di-tert-butylenetriamine; triethylenetetramine, tripropylenetetramine, triisopropylenetetramine, tributylenetetramine, tri-sec-butylenetetramine, triisobutylenetetramine and tri-tert-butylenetetramine; tetraethylenepentamine, tetrapropylenepentamine, tetraisopropylenepentamine, tetrabutylenepentamine, tetraisobutylenepentamine, tetra-sec-butylenepentamine and tetra-tert-butylenepentamine.

20. An improved process according to claim 16 wherein the additional nitrogen source is selected from the group consisting of ammonia, methylamine, ethylamine, n-propylamine, isopropylamine, n-butylamine, isobutylamine, sec-butylamine, tert-butylamine, pentylamine, pentyl-2-amine, pentyl-3-amine, n-hexylamine, n-heptylamine, n-octylamine, n-nonylamine, n-decylamine and 2-ethylhexylamine; ethylenediamine, propylenediamine, isopropylenediamine, butylenediamine, sec-butylenediamine, isobutylenediamine and tert-butylenediamine; diethylenetriamine, dipropylenetriamine, diisopropylenetriamine, dibutylenetriamine, diisobutylenetriamine, di-sec-butylenetriamine and di-tert-butylenetriamine; triethylenetetramine, tripropylenetetramine, triisopropylenetetramine, tributylenetetramine, tri-sec-butylenetetramine, triisobutylenetetramine and tri-tert-butylenetetramine; tetraethylenepentamine, tetrapropylenepentamine, tetraisopropylenepentamine, tetrabutylenepentamine, tetraisobutylenepentamine, tetra-sec-butylenepentamine and tetra-tert-butylenepentamine.

* * * * *